United States Patent [19]

Tomiya et al.

[11] Patent Number: 5,290,949
[45] Date of Patent: Mar. 1, 1994

[54] METHOD FOR PREPARING PYRROLIDINE DERIVATIVES

[75] Inventors: Kanji Tomiya; Koichi Moriyasu; Harumichi Aoki, all of Mobara; Kengo Oda, Hiratsuka, all of Japan

[73] Assignee: Mitsui Toatsu Chemicals, Incorporated, Tokyo, Japan

[21] Appl. No.: 997,369

[22] Filed: Dec. 24, 1992

[30] Foreign Application Priority Data

Dec. 25, 1991 [JP] Japan .................... 3-342890

[51] Int. Cl.$^5$ .......................... C07D 207/26
[52] U.S. Cl. ...................... 548/543; 504/283
[58] Field of Search ..................... 548/543

[56] References Cited

U.S. PATENT DOCUMENTS

| | | | |
|---|---|---|---|
| 4,110,105 | 8/1978 | Teach | 71/95 |
| 4,874,422 | 10/1989 | Woolard | 71/95 |
| 4,960,457 | 10/1990 | Woolard | 548/543 X |

FOREIGN PATENT DOCUMENTS 0134564 3/1985 European Pat. Off. .
0387869 9/1990 European Pat. Off. .

*Primary Examiner*—David B. Springer
*Attorney, Agent, or Firm*—Millen, White, Zelano & Branigan

[57] ABSTRACT

The present invention is directed to a method for preparing 3,4-trans-4-ethyl-1,3-disubstituted (substituted phenyl)pyrrolidine-2-one represented by the formula (1)

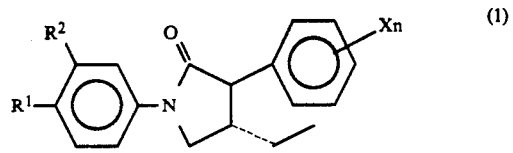

which comprises the steps of dissolving 4-ethyl-1,3-disubstituted (substituted phenyl)-3-pyrroline-2-one in an inert solvent, and then reducing the same with sodium boron hydride in the presence of methanol.

7 Claims, No Drawings

METHOD FOR PREPARING PYRROLIDINE DERIVATIVES

BACKGROUND OF THE INVENTION (a) Field of the Invention

The present invention relates to a method for preparing a pyrrolidine derivative represented by the formula (1)

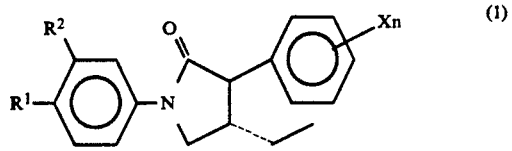

(wherein $R^1$ is a hydrogen atom, halogen atom or methyl group; $R^2$ is a hydrogen atom, alkyl group having 1 to 3 carbon atoms, trifluoromethyl group, haloalkoxy group having 1 to 3 carbon atoms, alkoxy group having 1 to 4 carbon atoms, nitro group, cyano group, phenoxy group, hydroxyl group or halogen atom; X is a hydrogen atom, halogen atom, trifluoromethyl group, alkyl group having 1 to 3 carbon atoms, cyano group or nitro group; and n is 1 or 2 and denotes the number of substituents represented by X, and in the case of n=2, the substituents of X may be identical or different, but $R^1$, $R^2$ and Xn are not simultaneously hydrogen).

3,4-trans-4-ethyl-1,3-disubstituted (substituted phenyl)pyrrolidine-2-one represented by this formula has a herbicidal activity.

(b) Description of the Prior Art

It has already been disclosed that certain kinds of pyrrolidine-2-one derivatives have a herbicidal activity (U.S. Pat. No. 4,110,105, EP-A-134,564, U.S. Pat. No. 4,874,422 and U.S. Pat. No. 4,960,457). Thus, 3-chloro-4-chloromethyl-1-(3-trifluoromethylphenyl)pyrrolidine-2-one (general name "flurochloridone") is on the market as a herbicide. In EP 387,869, there are described parts of compounds which can be prepared by the method of the present invention.

These compounds can all be manufactured by a radical cyclizing reaction using tributyltin hydride, and in this case, the pyrrolidine-2-one derivative is obtained as a mixture of a 3,4-trans isomer and a cis isomer. Since the 3,4-trans isomer only has the herbicidal activity, this known method is not preferable as a manufacturing process of the herbicidal compound.

A compound represented by the formula (1) can be obtained by subjecting a compound represented by the formula (2)

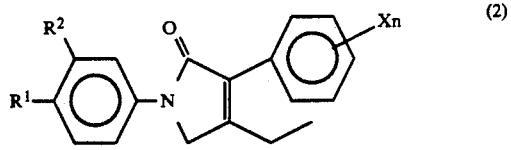

(wherein $R^1$, $R^2$, X and n are as defined above) to a catalytic hydrogenation reaction using palladium, platinum or the like as a catalyst. However, this reaction is not preferable, because when a chlorine atom or bromine atom is present in a substituent on the benzene ring, the elimination reaction of this halogen atom occurs together with the reduction of a double bond a the 3 and 4 positions of 3-pyrroline-2-one and it is very difficult to separate the desired compound.

Among the compounds represented by the formula (1), only compounds in which a steric configuration at the 3 and 4 positions of the pyrrolidine-2-one is in the trans state have the herbicidal activity. In the catalytic hydrogenation reaction using the metallic catalyst, the cis isomer is only obtained. In order to obtain the trans isomer, it is necessary to further carry out isomerization by the use of a base, which involves one more process step. Since this isomerization is an equilibrium reaction, the cis isomer partially remains in the obtained reaction product, and therefore this known technique is unsatisfactory as the preparation method of the compound for the herbicide.

SUMMARY OF THE INVENTION

An object of the present invention is to provide a method for simply and inexpensively preparing 3,4-trans-4-ethyl-1,3-disubstituted (substituted phenyl)pyrrolidine-2-one represented by the formula (1).

Investigation has been intensively made to solve the above-mentioned problems, and as a result, a preparation method which will be described hereinafter has been found. On the basis of this knowledge, the present invention has now been completed.

That is, the present invention is directed to a method for preparing 3,4-trans-4-ethyl-1,3-disubstituted (substituted phenyl)pyrrolidine-2-one represented by the above-mentioned formula (1) which comprises the step of reducing 4-ethyl-1,3-disubstituted (substituted phenyl)-3-pyrroline-2-one represented by the above-mentioned formula (2) with sodium boron hydride in the presence of methanol in an inert solvent.

According to the preparation method of the present invention, 3,4-trans-4-ethyl-1,3-disubstituted (substituted phenyl)pyrrolidine-2-one which is useful as the herbicide can be prepared in a high yield. Furthermore, the herbicide containing 3,4-trans-4-ethyl-1,3-disubstituted (substituted phenyl)pyrrolidine-2-one exerts a herbicidal activity to various weeds in paddy fields in small doses when administered before the emergence of the weeds or within their growth period. In addition, the herbicide shows excellent selectivity to paddy-field rice, and so it can be used safely.

DETAILED DESCRIPTION OF THE INVENTION

The present invention is directed to a method for preparing 3,4-trans-4-ethyl-1,3-disubstituted (substituted phenyl)pyrrolidine-2-one represented by the formula (1)

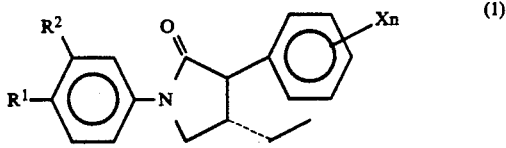

(wherein $R^1$ is a hydrogen atom, halogen atom or methyl group; $R^2$ is a hydrogen atom, alkyl group having 1 to 3 carbon atoms, trifluoromethyl group, haloalkoxy group having 1 to 3 carbon atoms, alkoxy group having 1 to 4 carbon atoms, nitro group, cyano group, phenoxy group, hydroxyl group or halogen atom; X is a hydrogen atom, halogen atom, trifluoromethyl group, alkyl group having 1 to 3 carbon atoms, cyano group or nitro group; and n is 1 or 2 and denotes the number of substituents represented by X, and in the case of n=2, the substituents of X may be identical or different, but R¹, R² and Xn are not simultaneously hydrogen atoms) which comprises the step of reducing 4-ethyl-1,3-disubstituted (substituted phenyl)-3-pyrroline-2-one represented by the formula (2)

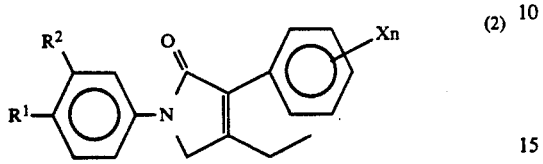

(wherein R¹, R², X and n are as defined above) with sodium boron hydride in the presence of methanol in an inert solvent.

The above-mentioned reducing reaction can be achieved by adding sodium boron hydride to 4-ethyl-1,3-disubstituted (substituted phenyl)-3-pyrroline-2-one represented by the above-mentioned formula (2) dissolved in the inert solvent, and then slowly adding methanol thereto under heating. The amount of sodium boron hydride which is used in the reaction is in the range of from 0.5 to 1.0 mol, preferably from 0.6 to 0.8 mol per mol of 4-ethyl-1,3-disubstituted (substituted phenyl)-3-pyrroline-2-one of the formula (2). The amount of methanol to be added is in the range of from 0.2 to 2.0 ml, preferably from 0.5 to 1.0 ml per mmol of sodium boron hydride. Examples of the inert solvent which is used in the reaction include hydrocarbons such as benzene, toluene and xylene; ethers such as tetrahydrofuran, diethyl ether and dioxane; and tert-butyl alcohol. Above all, tetrahydrofuran and tert-butyl alcohol are particularly preferable. The reaction temperature is in the range of from room temperature to the reflux temperature of the reaction solvent, and the particularly preferable temperature is from 50° to 70° C. The reaction time depends upon the reaction temperature and the addition speed of methanol, but it is in the range of from 1 to 20 hours.

4-ethyl-1,3-disubstituted (substituted phenyl)-3-pyrroline-2-one represented by the above-mentioned formula (2) which is the starting material in the preparation method of the present invention can be prepared in accordance with the following reaction formula A.

Reaction formula A:

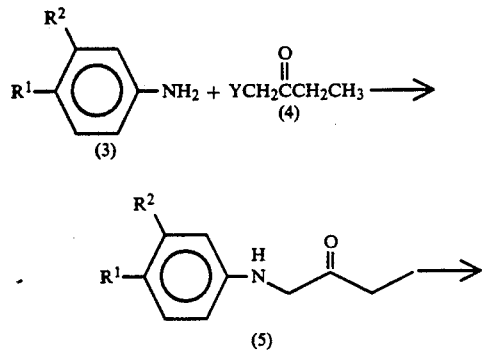

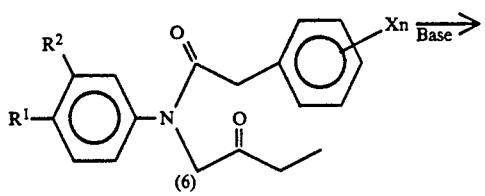

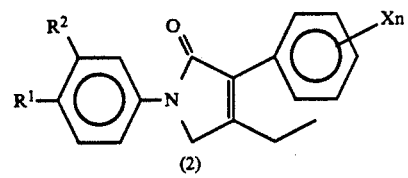

(wherein R¹, R², X and n are as defined above, and Y is a halogen atom).

A 3,4-disubstituted aniline represented by the formula (3) is reacted with a haloketone represented by the formula (4) to obtain a ketoaniline derivative represented by the formula (5). Next, this ketoaniline derivative is acylated with an Xn-substituted phenylacetyl halide (X and n are as defined above) to obtain a carbonyl derivative represented by the formula (6), and the thus obtained carbonyl derivative is then treated with a base to carry out an intramolecular aldol condensation, thereby obtaining 4-ethyl-1,3-disubstituted (substituted phenyl)-3-pyrroline-2-one of the formula (2).

These reactions will be described in more detail. The 3,4-disubstituted aniline of the formula (3) is reacted with the haloketone of the formula (4) in the presence of the base to obtain the ketoaniline derivative of the formula (5). Examples of the base include organic bases such as triethylamine, diisopropylethylamine and pyridine; inorganic bases such as sodium carbonate, potassium carbonate, cesium carbonate, sodium hydroxide and potassium hydroxide; metal alcoholates such as potassium-tert-butoxide, sodium methoxide and sodium ethoxide; and metal hydrides such as sodium hydride and lithium hydride.

Examples of the solvent include hydrocarbons such as benzene and toluene; alcohols such as methanol and ethanol; and non-protonic polar solvents such as N,N-dimethylformamide and dimethyl sulfoxide.

The reaction temperature is from 30° to 120° C., particularly preferably from 40° to 50° C. The reaction time depends upon the reaction temperature, but it is in the range of from 2 to 15 hours.

The thus obtained ketoaniline derivative of the formula (5) is reacted with the Xn-substituted phenylacetyl halide in the presence of a base to obtain a carbonyl derivative of the formula (6). Examples of the base include organic bases such as triethylamine, diisopropylethylamine and pyridine; and inorganic bases such as sodium carbonate, potassium carbonate, cesium carbonate, sodium hydroxide and potassium hydroxide.

Examples of the solvent include hydrocarbons such as benzene and toluene; alcohols such as methanol and ethanol; and non-protonic polar solvents such as N,N-dimethylformamide and dimethyl sulfoxide.

The reaction temperature is from 30° to 120° C., particularly preferably from 20° to 40° C. The reaction time depends upon the reaction temperature, but it is in the range of from 2 to 5 hours.

The thus obtained carbonyl derivative of the formula (6) is then treated with the base to carry out the intramolecular aldol condensation, thereby obtaining 4-ethyl-1,3-disubstituted (substituted phenyl)-3-pyrroline-2-one of the formula (2). Examples of the base include metal alcoholates such as potassium-tert-butoxide, sodium methoxide and sodium ethoxide; metal hydrides such as sodium hydride and lithium hydride; and inorganic bases such as sodium hydroxide and potassium hydroxide.

Examples of the solvent include hydrocarbons such as benzene and toluene; alcohols such as methanol and ethanol; non-protonic polar solvents such as N,N-dimethylformamide and dimethyl sulfoxide; and ethers such as tetrahydrofuran.

The reaction temperature is from 10° to 70° C., particularly preferably from 20° to 40° C. The reaction time depends upon the reaction temperature, but it is in the range of from 0.5 to 2 hours.

In this serial reaction, the reactions of the two steps which obtain the carbonyl derivative of the formula (6) from 3,4-disubstituted aniline of the formula (3) can also be continuously carried out in one reaction vessel without isolating an intermediate.

The carbonyl derivative represented by the formula (6) can also be prepared in accordance with the following reaction formula B:

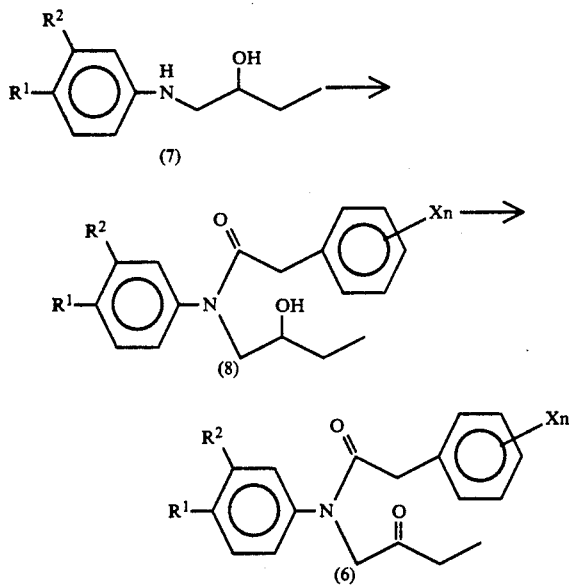

A hydroxyaniline derivative represented by the formula (7) is treated with an Xn-substituted phenylacetyl halide to selectively acylate an amino group only, whereby an amide derivative represented by the formula (8) is obtained. Next, this product is oxidized to obtain a carbonyl derivative represented by the formula (6).

The hydroxyaniline derivative of the formula (7) is reacted with the above-mentioned acid halide corresponding to the formula (8) in the presence of the base to obtain the amide derivative of the formula (8). In order to selectively carry out the acylation to the amino group, it is preferable to use a hydrocarbon such as toluene or benzene as the solvent and to use pyridine or triethylamine as the base, and the reaction temperature is preferably from a level under ice cooling to 100° C.

More preferably, toluene and pyridine are used as the solvent and the base, respectively, and the reaction temperature is from 50° to 70° C.

The thus obtained amide derivative of the formula (8) is oxidized to obtain the carbonyl derivative of the formula (6). This oxidizing reaction can be achieved by the use of a heavy metal salt such as pyridinium dichromate or pyridinium chlorochromate, or a usual oxidizing agent such as sodium hypochlorite.

Furthermore, the hydroxyaniline derivative of the formula (7) can be obtained in accordance with a reaction of a corresponding aniline with 1,2-butylene oxide, as shown by the following reaction formula C:

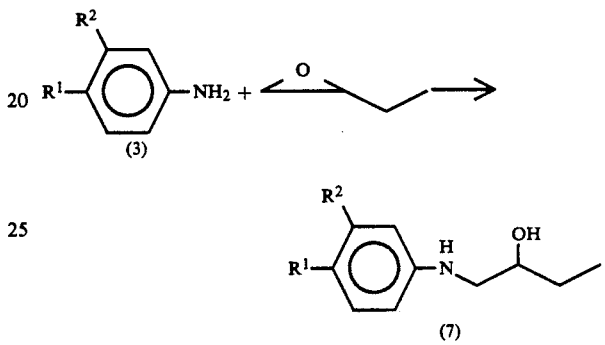

Now, the present invention will be described in detail in reference to examples.

EXAMPLE 1

Synthesis of N-(3-isopropylphenyl)-N-(2-hydroxybutyl)-3-chlorophenylacetamide 8.9 g (42.9 mmol) of N-(2-hydroxybutyl)-m-isopropylaniline were dissolved in 50 ml of toluene, and 5 ml of pyridine were then added thereto. Next, 8.11 g (42.9 mmol) of m-chlorophenylacetyl chloride were added dropwise thereto, while the temperature of the solution was maintained at 50° C. or less. After stirred for 1 hour at this temperature, the reaction mixture was poured into water, and then extracted with ethyl acetate. The resultant organic layer was washed with water, 1 N hydrochloric acid, water, an aqueous saturated sodium bicarbonate and water in this order, followed by drying over anhydrous magnesium sulfate. The solvent was distilled off under reduced pressure, and the solution was then purified through silica gel column chromatography (an eluent: hexane/ethyl acetate =7/3) to obtain 12.8 g of the desired product in an oily state (yield: 83.2%).

IR $\nu$ cm$^{-1}$: 3424, 1647

NMR (CDCl$_3$) $\delta$ ppm: 0.90 (3H, t, J=7.3Hz), 1.23 (6H, d, J=7.4Hz), 1.44 (2H, m), 1.78 (1H, bs), 2.86 (1H, m), 3.37 (2H, m), 3.43 (2H, s), 3.75 (1H, m), 4.11 (2H, m), 6.93–7.01 (4H, m), 7.18 (2H, m), 7.25 (1H, m), 7.33 (1H, m)

The synthetic process of the starting material for use in the above-mentioned reaction will be described for reference as follows.

REFERENCE EXAMPLE 1

Synthesis of N-(2-hydroxybutyl)-m-isopropylaniline 10 g (74 mmol) of m-isopropylaniline were dissolved in 100 ml of methanol, and 6.4 g (88.8 mmol) of 1,2-butylene oxide were added thereto. Next, the solution was heated up to 50° C., and then stirred for 1 hour. The solvent was distilled off under reduced pressure, and the solution was then purified through silica gel column chromatography [an eluting solvent: hexane/ethyl acetate=7/3 (v/v)] to obtain 13.2 g of the desired product in an oily state (yield: 86.2%).

EXAMPLE 2

Synthesis of N-(3-isopropylphenyl)-N-(2-oxobutyl)-3-chlorophenylacetamide 15.7 g (41.7 mmol) of pyridinium dichromate were dissolved in 80 ml of methylene chloride, and 1.4 ml of trifluoroacetic acid and 0.9 ml of pyridine were added thereto. Next, 10 ml of a methylene chloride solution containing 10.0 g (27.8 mmol) of N-(3-isopropylphenyl)-N-(2-hydroxybutyl)-3-chlorophenylacetic amide obtained in Example 1 were added dropwise to the solution, while refluxed and stirred. Reaction was then carried out at the same temperature for 4 hours, and the resultant reaction mixture was then poured into 200 ml of diethyl ether. Insolubles were removed by filtration and the solvent was distilled off under reduced pressure, and the solution was then purified through silica gel column chromatography (an eluent: hexane/ethyl acetate=7/3) to obtain 7.61 g of the desired product in an oily state (yield: 76.2%).

IR $\nu$ cm$^{-1}$: 1732, 1660

NMR (CDCl$_3$) δ ppm: 1.08 (3H, t, J=7.3Hz), 1.25 (6H, d, J=6.60Hz), 2.45 (2H, m), 2.85 (1H, m), 3.50 (2H, s), 4.40 (2H, s), 7.01 (2H, m), 7.09 (2H, m), 7.15 (2H, m), 7.31 (1H, m), 7.37 (1H, m)

EXAMPLE 3

Synthesis of N-(3-isopropylphenyl)-N-(2-oxobutyl)-3-chlorophenylacetamide 200 g (1.48 mol) of m-isopropylaniline were dissolved in 600 ml of toluene, and 284 ml of diisopropylethylamine were then added thereto. The solution was heated to 45° C. under a nitrogen stream, and 245.8 g (1.63 mols) of bromomethyl ethyl ketone were added dropwise over 3 hours. After the temperature of the solution was returned to room temperature, 132 ml of pyridine were added thereto, and 308 g (1.63 mols) of m-chlorophenylacetyl chloride were then added dropwise thereto. The reaction mixture was poured into water, and the resultant organic layer was separated, washed with an aqueous saturated sodium bicarbonate solution and water in this order, and then dried over magnesium sulfate. The solvent was distilled off under reduced pressure to obtain 492.8 g of a crude product in an oily state (yield: 93.0%).

IR $\nu$ cm$^{-1}$: 1732, 1660

NMR (CDCl$_3$) δ ppm: 1.08 (3H, t, J=7.3Hz), 1.25 (6H, d, J=6.60Hz), 2.45 (2H, m), 2.85 (1H, m), 3.50 (2H, s), 4.40 (2H, s), 7.01 (2H, m), 7.09 (2H, m), 7.15 (2H, m), 7.31 (1H, m), 7.37 (1H, m)

EXAMPLE 4

Synthesis of 4-ethyl-3-(3-chlorophenyl)-1-(3-isopropylphenyl)-3-pyrroline-2-one 7.61 g (21.3 mmol) of N-(3-isopropylphenyl)-N-(2-oxobutyl)-3-chlorophenylacetamide synthesized in Example 2 or 3 were dissolved in 35 ml of ethanol, and 0.1 ml of an ethanol solution containing 30% of sodium ethoxide was added at room temperature with stirring. The solution was successively stirred at the same temperature for 2 hours, and the resultant reaction mixture was poured into water, followed by extraction with ethyl acetate. The solvent was distilled off under reduced pressure, and the solution was then purified through silica gel column chromatography (an eluent: hexane/ethyl acetate=4/1) to obtain 5.9 g of the desired product in an oily state (yield: 77.5%).

IR $\nu$ cm$^{-1}$: 1691

NMR (CDCl$_3$) δ ppm: 1.25 (3H, t, J=7.3Hz), 1.28 (H, d, J=7.4Hz), 2.64 (2H, q, J=7.3Hz), 2.93 (1H, m), 4.42 (2H, s), 7.00 (1H, m), 7.21-7.39 (4H, m), 7.55 (2H, m), 7.76 (1H, m)

EXAMPLE 5

Synthesis of 1 (4-chloro-3-trifluoromethylphenyl)-4-ethyl-3-(3-fluorophenyl)-3-pyrroline-2-one 2.38 g (5.92 mmol) of N-(4-chloro-3-trifluoromethylphenyl)-N-(2-oxobutyl)-3-fluorophenylacetamide prepared in the same manner as in Example 3 were dissolved in 10 ml of ethanol, and 0.25 ml of a 10% aqueous sodium hydroxide solution was added at room temperature with stirring. The solution was stirred at the same temperature for 1 hour, and the reaction mixture was then poured into water, followed by extraction with ethyl acetate. Afterward, the resultant organic layer was dried over magnesium sulfate, and the solvent was then distilled off under reduced pressure. The precipitated crystals were collected by filtration, and then washed with n-hexane to obtain 1.93 g of the desired product in the state of colorless crystals (yield: 85.0%).

m.p. 125.8°-128.8° C.

IR $\nu$ cm$^{-1}$: 1687

NMR (CDCl$_3$) δ ppm: 1.27 (3H, t, J=7.3Hz), 2.67 (2H, q, j=7.3Hz), 4.42 (2H, s), 7.08 (1H, m), 7.16-7.23 (2H, m), 7.41 (1H, m), 7.50 (1H, m), 8.00 (1H, m), 8.00 (1H, s)

EXAMPLE 6

Synthesis of 4-ethyl-3-(3-fluorophenyl)-1-(3-trifluoromethylphenyl)-3-pyrroline-2-one 2.74 g (7.47 mmol) of N-(3-trifluoromethylphenyl)-N-(2-oxobutyl)-3-fluorophenylacetamide synthesized in the same manner as in Example 3 were dissolved in 30 ml of ethanol, and 0.05 ml of an ethanol solution containing 30% of sodium ethoxide was added thereto at room temperature with stirring. The solution was stirred at the same temperature for 2 hours, and the resultant reaction mixture was then poured into water, followed by extraction with ethyl acetate. Afterward, the resultant organic layer was dried over magnesium sulfate, and the solvent was distilled off under reduced pressure. The precipitated crystals were collected by filtration, and then washed with diethyl ether to obtain 2.15 g of the desired product in the state of colorless crystals (yield: 82.4%).

m.p. 77.5°-79.0° C.

IR $\nu$ cm.$^{-1}$: 1690

NMR (CDCl$_3$) δ ppm: 1.25 (3H, t, J=7.3Hz), 2.66 (2H, q, j=7.3Hz), 2.43 (2H, s), 6.92-7.10 (3H, m), 7.30-7.60 (3H, m), 7.90-8.00 (2H, m).

The following compounds were synthesized in the same manner as in Examples 4-6.

3-(3-chlorophenyl)-4-ethyl-1-(3-trifluorophenyl)-3-pyrroline-2-one

IR ν cm⁻¹: 1690

NMR (CDCl₃) δ ppm: 1.29 (3H, t, J=8.0Hz), 2.68 (2H, q, H=8.0Hz), 4.46 (2H, s), 7.31–7.53 (6H, m), 8.02–8.07 (2H, m)

4-ethyl-1-(3-trifluorophenyl)-3-(3-methylphenyl)-3-pyrroline-2-one

IR ν cm⁻¹: 1691

NMR (CDCl₃) δ ppm: 1.23 (3H, t, J=8.1Hz), 2.40 (3H, s), 2.67 (2H, q, H=8.1Hz), 4.42 (2H, s), 7.15–7.52 (6H, m), 8.03–8.07 (2H, m)

4-ethyl-1-(3-trifluorophenyl)-3-(3-methoxyphenyl)-3-pyrroline-2-one

IR ν cm⁻¹: 1693

NMR (CDCl₃) δ ppm: 1.24 (3H, t, J=7.9Hz), 2.68 (2H, q, H=7.9Hz), 3.82 (3H, s), 4.43 (2H, s), 6.89–7.04 (3H, m), 7.34–7.38 (2H, m), 7.50 (1H, m), 8.00–3.10 (2H, m)

EXAMPLE 7

Synthesis of 4-ethyl-3-(3-chlorophenyl)-1-(3-isopropylphenyl)pyrrolidine-2-one (Compound No. 41)

5.0 g (14.7 mmol) of 4-ethyl-3-(3-chlorophenyl)-1-(3-isopropylphenyl)-3-pyrroline-2-one synthesized in Example 4 and 0.56 g (14.7 mmol) of sodium boron hydride were dissolved in 70 ml of tetrahydrofuran, and 11 ml of methanol were slowly added to the solution over about 1 hour, while the solution was heated under reflux. Reaction was allowed to proceed at the same temperature for further 1 hour, and the reaction mixture was then poured into 1 N hydrochloric acid, followed by extraction with ethyl acetate. The resultant organic layer was washed with water, an aqueous saturated sodium bicarbonate solution and water in this order, and then dried over magnesium sulfate. The solvent was distilled off under reduced pressure, and n-hexane was then added to the resultant residue to achieve crystallization, followed by recrystallization from etherpetroleum ether, thereby obtaining 4.5 g of the desired product in the state of colorless crystals (yield 90%). m.p. 88.5°–90.0° C.

EXAMPLE 8

Synthesis of 1-(4-chloro-3-trifluoromethylphenyl)-4-ethyl-3-(3-fluorophenyl)pyrrolidine-2-one (Compound No. 17)

14.0 g (36.4 mmol) of 1-(4-chloro-3-trifluoromethylphenyl)-4-ethyl-3-(3-fluorophenyl) -3-pyrroline-2-one synthesized in Example 5 and 1.10 g (29.1 mmol) of sodium boron hydride were dissolved in 120 ml of tetrahydrofuran, and 22 ml of methanol were slowly added to the solution over about 1.5 hours, while the solution was heated under reflux. Reaction was allowed to proceed at the same temperature for further 1 hour, and the reaction mixture was then poured into 1 N hydrochloric acid, followed by extraction with ethyl acetate. The resultant organic layer was washed with water, an aqueous saturated sodium bicarbonate solution and water in this order, and then dried over magnesium sulfate. The solvent was distilled off under reduced pressure, and n-hexane was then added to the resultant residue to achieve crystallization, followed by recrystallization from ether-n-hexane, thereby obtaining 13.4 g of the desired product in the state of colorless crystals (yield 95%).

m.p 131.3°–133.2° C.

EXAMPLE 9

Synthesis of 4-ethyl-3-(3-fluorophenyl)-1-(3-trifluoromethylphenyl)pyrrolidine-2-one (Compound No. 3)

28.0 g (79.9 mmol) of 4-ethyl-3-(3-fluorophenyl)-1-(3-trifluoromethylphenyl)-3-pyrroline -2-one synthesized in Example 6 and 2.56 g (67.6 mmol) of sodium boron hydride were dissolved in 200 ml of tetrahydrofuran, and 50 ml of methanol were slowly added to the solution over about 2 hours, while the solution was heated under reflux. Reaction was allowed to proceed at the same temperature for further 1 hour, and the reaction mixture was then poured into 1 N hydrochloric acid, followed by extraction with ethyl acetate. The resultant organic layer was washed with water, an aqueous saturated sodium bicarbonate solution and water in this order, and then dried over magnesium sulfate. The solvent was distilled off under reduced pressure, and n-hexane was then added to the resultant residue to achieve crystallization, followed by recrystallization from ether-n-hexane, thereby obtaining 26.1 g of the desired product in the state of colorless crystals (yield 92.9%). m.p. 98.5°–100.0° C.

Examples of the compounds represented by the formula (1) which can be prepared in accordance with the preparation method of the present invention will be enumerated in Table 1.

TABLE 1

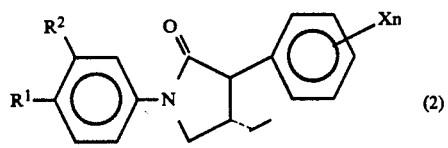

(2)

| Compound No. | Substituents of General Formula (2) | | | Values of Physical Properties |
|---|---|---|---|---|
| | R₁ | R₂ | Xn | |
| 1 | H | CF₃ | H | NMR(100MHz, CDCl₃)δ ppm: 1.00(3H, t, J=7Hz), 1.50–1.90(2H, m), 2.30–2.80 (1H, m), 3.54(1H, d, J=10Hz), 3.61(1H, t, J=8Hz), 4.06(1H, dd, J=8Hz, 9Hz), 7.20–7.75(7H, m), 7.95–8.15(2H; m) IRνneat cm⁻¹: 1700 |
| 2 | H | CF₃ | 4-F | NMR(100MHz, CDCl₃)δ ppm: 1.00(3H, t, J=7Hz), 1.45–1.90(2H, m), 2.20–2.65 (1H, m), 3.49(1H, d, J=10Hz), 3.58(1H, t, J=8Hz), 4.03(1H, dd, J=8Hz, 9Hz), 6.96–7.37(4H, m), 7.40–7.60(2H, m), 7.80–8.05(2H, m) |

TABLE 1-continued

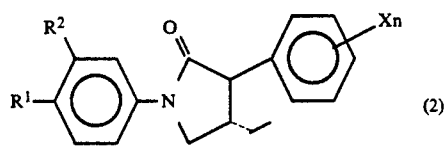

(2)

| Compound No. | Substituents of General Formula (2) | | | Values of Physical Properties |
|---|---|---|---|---|
| | R₁ | R₂ | Xn | |
| 3 | H | CF₃ | 3-F | IRνnujol cm⁻¹: 1700  m.p. 82–84.0° C.<br>NMR(270MHz, CDCl₃)δ ppm: 0.99(3H, t, J=7.6Hz), 1.49–1.60(1H, m), 1.70–1.81 (1H, m), 2.41–2.56(1H, m), 3.51(1H, d, J=10.5Hz), 3.60(1H, t, J=9.5Hz), 4.04(1H, dd, J=7.8Hz, 9.5Hz), 6.97–7.07(3H, m), 7.31–7.53(3H, m), 7.93–7.96(2H, m) |
| 4 | H | CF₃ | 4-CF₃ | IRνnujol cm⁻¹: 1700  m.p. 98.5–100.0° C.<br>NMR(270MHz, CDCl₃)δ ppm: 0.99(3H, t, J=7.5Hz), 1.50–1.66(1H, m), 1.68–1.85 (1H, m), 2.45–2.58(1H, m), 3.58(1H, d, J=10.3Hz), 3.63(1H, t, J=9.5Hz), 4.06(1H, dd, J=7.3Hz, 9.5Hz), 7.40(2H, d, J=7.8Hz), 7.44–7.56(2H, m), 7.65(2H, d, J=7.8Hz), 7.87–7.96(2H, m) |
| 5 | H | CF₃ | 3-CF₃ | IRνnujol cm⁻¹: 1700  m.p. 94.5–96.4° C.<br>NMR(270MHz, CDCl₃)δ ppm: 0.99(3H, t, J=7.3Hz), 1.48–1.62(1H, m), 1.70–1.82 (1H, m), 2.43–2.59(1H, m), 3.58(1H, d, J=10.5Hz), 3.63(1H, t, J=9.5Hz), 4.06(1H, dd, J=7.8Hz, 9.5Hz), 7.36–7.60(6H, m), 7.92–7.97(2H, m). |
| 6 | H | CF₃ | 3-Cl | IRνnujol cm⁻¹: 1700  m.p. 87.0–88.5° C.<br>NMR(270MHz, CDCl₃)δ ppm: 0.99(3H, t, J=7.6Hz), 1.48–1.65(1H, m), 1.70–1.85 (1H, m), 2.40–2.55(1H, m), 3.49(1H, d, J=10.3Hz), 3.60(1H, t, J=9.5Hz), 4.03(1H, dd, J=7.6Hz, 9.5Hz), 7.10–7.19(1H, m), 7.25–7.50(5H, m), 7.92–7.97(2H, m). |
| 7 | H | CF₃ | 3,5-F₂ | IRνnujol cm⁻¹: 1705  m.p. 105.9–106.8° C.<br>NMR(270MHz, CDCl₃)δ ppm: 0.97(3H, t, J=7.6Hz), 1.50–1.67(1H, m), 1.70–1.85 (1H, m), 2.40–2.55(1H, m), 3.50(1H, d, J=10.5Hz), 3.61(1H, t, J=9.5Hz), 4.04(1H, dd, J=7.8Hz, 9.5Hz), 6.73–6.86(3H, m), 7.41–7.54(2H, m), 7.89–7.96(2H, m). |
| 8 | H | CF₃ | 3,4-F₂ | IRνKBr cm⁻¹: 1690  m.p. 88.2–89.7° C.<br>NMR(270MHz, CDCl₃)δ ppm: 0.96(3H, t, J=7.3Hz), 1.46–1.66(1H, m), 1.70–1.85 (1H, m), 2.37–2.49(1H, m), 3.47(1H, d, J=10.8Hz), 3.60(1H, t, J=9.5Hz), 4.03(1H, dd, J=7.8Hz, 9.5Hz), 6.97–7.23(3H, m), 7.41–7.54(2H, m), 7.91-(2H, m) |
| 9 | H | CF₃ | 3-CH₃ | IRνnujol cm⁻¹: 1700  m.p. 76.5–80.5° C.<br>NMR(270MHz, CDCl₃)δ ppm: 0.95(3H, t, J=7.9Hz), 1.48–1.68(1H, m), 1.70–1.85 (1H, m), 2.37(3H, s), 2.41–2.56(1H, m), 3.46(1H, d, J=10.4Hz), 3.58(1H, t, J=8.9Hz), 4.04(1H, dd, J=7.9Hz, 8.9Hz), 7.04–7.13(3H, m), 7.21–7.32(1H, m), 7.42–7.53(2H, m), 7.89–7.99(2H, m) |
| 10 | H | CF₃ | 2,4-F₂ | IRνneat cm⁻¹: 1700<br>NMR(270MHz, CDCl₃)δ ppm: 0.98(3H, t, J=7.6Hz), 1.51–1.80(2H, m), 2.41–2.53 (1H, m), 3.60(1H, t, J=9.2Hz), 3.71(1H, d, J=10.8Hz), 4.03(1H, dd, J=7.9Hz, 9.2Hz), 6.80–6.92(2H, m), 7.15–7.25(1H, m), 7.38–7.55(2H, m), 7.80–8.00(2H, m) |
| 11 | H | CF₃ | 3,5-Cl₂ | IRνneat cm⁻¹: 1690<br>NMR(270MHz, CDCl₃)δ ppm: 1.00(3H, t, J=7.4Hz), 1.50–1.82(2H, m), 2.43–2.51 (1H, m), 3.46(1H, d, J=10.9Hz), 3.60(1H, t, J=8.9Hz), 4.04(1H, t, J=8.9Hz), 7.16(2H, d, J=1.5Hz), 7.29–7.35(1H, m), 7.42–7.54(2H, m), 7.89–7.96(2H, m) |
| 12 | H | CF₃ | 2,3-Cl₂ | IRνneat cm⁻¹: 1700<br>NMR(270MHz, CDCl₃)δ ppm: 0.98(3H, t, J=7.4Hz), 1.45–1.80(2H, m), 2.52–2.63 (1H, m), 3.64(1H, t, J=8.9Hz), 4.03(1H, d, J=9.5Hz), 4.08(1H, t, J=8.9Hz), 7.14(1H, dd, J=1.5Hz, 7.9Hz), 7.22(1H, dd, J=1.5Hz, 7.9Hz), 7.42–7.46(2H, m), 7.51(1H, t, J=7.9Hz), 7.91–7.98(2H, m) |
| 13 | H | CF₃ | 3-Br | IRνneat cm⁻¹: 1700<br>NMR(270MHz, CDCl₃)δ ppm: 0.98(3H, t, J=7.4Hz), 1.48–1.85(2H, m), 2.40–2.55 (1H, m), 3.47(1H, d, J=10.3Hz), 3.59(1H, t, J=8.9Hz), 4.03(1H, dd, J=8.2Hz, 8.9Hz), 7.12–7.53(6H, m), 7.92–7.97(2H, m) |
| 14 | H | CF₃ | 4-Cl | IRνnujol cm⁻¹: 1700  m.p. 95.2–96.8° C.<br>NMR(270MHz, CDCl₃)δ ppm: 0.98(3H, t, J=7.3Hz), 1.48–1.82(2H, m), 2.38–2.52 (1H, m), 3.48(1H, d, J=10.3Hz), 3.59(1H, t, J=8.9Hz), 4.02(1H, t, J=8.9Hz), 7.15–7.27(3H, m), 7.32–7.52(3H, m), 7.88–7.97(2H, m) |
| 15 | H | CF₃ | 3-NO₂ | IRνneat cm⁻¹: 1700<br>NMR(270MHz, CDCl₃)δ ppm: 0.97(3H, t, J=7.4Hz), 1.55–1.83(2H, m), 2.50–2.65 (1H, m), 3.64(1H, d, J=9.2Hz), 3.66(1H, t, J=9.2Hz), 4.08(1H, dd, J=8.0Hz, 9.2Hz), 7.40–7.67(4H, m), 7.90–7.97(2H, m), 8.15–8.23(2H, m) |
| 16 | F | CF₃ | 3-F | IRνneat cm⁻¹: 1700<br>NMR(270MHz, CDCl₃)δ ppm: 0.99(3H, t, J=7.4Hz), 1.49–1.65(1H, m), 1.70–1.83 (1H, m), 2.43–2.54(1H, m), 3.50(1H, d, J=10.4Hz), 3.58(1H, t, J=9.4Hz), 4.00(1H, dd, J=7.8Hz, 9.4Hz), 6.95–7.08(3H, m), 7.16–7.39(2H, m), 7.86–7.97(2H, m) |
| 17 | Cl | CF₃ | 3-F | IRνnujol cm⁻¹: 1700  m.p. 116.6–117.8° C.<br>NMR(270MHz, CDCl₃)δ ppm: 0.96(3H, t, J=7.5Hz), 1.48–1.65(1H, m), 1.70–1.85 (1H, m), 2.40–2.55(1H, m), 3.50(1H, d, J=10.3Hz), 3.57(1H, t, J=9.1Hz), 4.01(1H, t, J=9.1Hz), 6.95–7.09(3H, m), 7.31–7.39(1H, m), 7.50(1H, d, J=8.9Hz), 7.90(1H, dd, J=8.9Hz, 2.4Hz), 8.00(1H, d, J=2.4Hz) |
| 18 | H | CF₃ | 3-CN | IRνnujol cm⁻¹: 1700  m.p. 131.3–133.2° C.<br>NMR(270MHz, CDCl₃)δ ppm: 0.99(3H, t, J=7.3Hz), 1.51–1.84(2H, m), 2.41–2.57 (1H, m), 3.56(1H, d, J=10.3Hz), 3.64(1H, t, J=9.5Hz), 4.06(1H, dd, J=7.8Hz, 9.5Hz), 7.42–7.64(6H, m), 7.85–7.95(2H, m) |
| 19 | H | CF₃O | 3-F | IRνnujol cm⁻¹: 2230, 1700  m.p. 113.0–115.5° C.<br>NMR(400MHz, CDCl₃)δ ppm: 1.02(3H, t, J=7.3Hz), 1.50–1.66(1H, m), 1.71–1.81 (1H, m), 2.41–2.52(1H, m), 3.50(1H, d, J=10.0Hz), 3.55(1H, t, J=8.8Hz), |

TABLE 1-continued

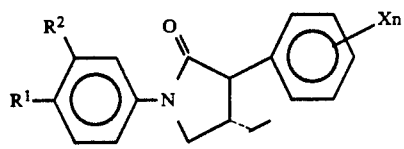

(2)

| Compound No. | Substituents of General Formula (2) R₁ | R₂ | Xn | Values of Physical Properties |
|---|---|---|---|---|
| | | | | 4.03(1H, t, J=8.8Hz), 6.96-7.05(4H, m), 7.30-7.42(2H, m), 7.62(1H, m), 7.68(1H, m) IRνneat cm⁻¹: 1705 |
| 20 | H | HCF₂O | 3-F | NMR(400MHz, CDCl₃)δ ppm: 0.97(3H, t, J=7.3Hz), 1.52-1.64(1H, m), 1.72-1.81 (1H, m), 2.42-2.49(1H, m), 3.49(1H, d, J=10.3Hz), 3.55(1H, t, J=8.8Hz), 4.00(1H, t, J=8.8Hz), 6.54(1H, t, J=74.0Hz), 6.91-7.05(4H, m), 7.32-7.38 (2H, m), 7.49(1H, dd, J=1.5Hz, 8.1Hz), 7.61(1H, m) IRνneat cm⁻¹: 1702 |
| 21 | H | CF₂BrO | 3-F | NMR(400MHz, CDCl₃)δ ppm: 0.98(3H, t, J=7.3Hz), 1.53-1.64(1H, m), 1.73-1.80 (1H, m), 2.44-2.51(1H, m), 3.50(1H, d, J=10.3Hz), 3.54(1H, t, J=9.5Hz), 4.01(1H, dd, J=8.0Hz, 9.5Hz), 6.96-7.07(4H, m), 7.32-7.43(2H, m), 7.64-7.69(2H, m) IRνneat cm⁻¹: 1707 |
| 22 | H | HCF₂CF₂O | 3-F | NMR(400MHz, CDCl₃)δ ppm: 0.98(3H, t, J=7.3Hz), 1.50-1.62(1H, m), 1.71-1.81 (1H, m), 2.41-2.51(1H, m), 3.49(1H, d, J=10.3Hz), 3.55(1H, t, J=9.5Hz), 4.00(1H, dd, J=8.1Hz, 9.5Hz), 5.90(1H, dt, J=2.9Hz, 53.0Hz), 6.96-7.05 (4H, m), 7.31-7.40(2H, m), 7.58-7.60(1H, m), 7.65(1H, d, J=2.2Hz) IRνneat cm⁻¹: 1703 |
| 23 | H | HCF₂CF₂O | 3-Cl | NMR(400MHz, CDCl₃)δ ppm: 0.98(3H, t, J=7.3Hz), 1.50-1.62(1H, m), 1.70-1.79 (1H, m), 2.41-2.51(1H, m), 3.47(1H, d, J=11.0Hz), 3.55(1H, t, J=9.5Hz), 4.00(1H, dd, J=8.1Hz, 9.5Hz), 5.90(1H, dt, J=2.9Hz, 53.0Hz), 7.04(1H, d, J=7.3Hz) 7.15(1H, m), 7.25-7.40(4H, m), 7.59(1H, dd, J=1.4Hz, 8.1Hz), 7.65(1H broad s) IRνneat cm⁻¹: 1702 |
| 24 | H | CH₃ | 3-Cl | NMR(400MHz, CDCl₃)δ ppm: 0.97(3H, t, J=7.3Hz), 1.51-1.59(1H, m), 1.71-1.78 (1H, m), 2.37(3H, s), 2.39-2.46(1H, m), 3.48(1H, d, J=10.3Hz), 3.57 (1H, t, J=8.8Hz), 3.99(1H, dd, J=8.1Hz, 9.5Hz), 6.96-7.06(4H, m), 7.24-7.34 (2H, m), 7.42(1H, d, J=8.1Hz), 7.54(1H, s) IRνKBr cm⁻¹: 1700 m.p. 81.0~84.0° C. |
| 25 | H | Cl | 3-F | NMR(400MHz, CDCl₃)δ ppm: 0.97(3H, t, J=7.3Hz), 1.51-1.60(1H, m), 1.70-1.80 (1H, m), 2.37(3H, s), 2.38-2.49(1H, m), 3.48(1H, d, J=9.8Hz), 3.53 (1H, t, J=9.3Hz), 3.97(1H, dd, J=8.3Hz, 9.3Hz), 6.95-7.04(3H, m), 7.13 (1H, d, J=8.3Hz), 7.28-7.36(2H, m), 7.61(1H, d, J=8.3Hz), 7.72(1H, s) IRνKBr cm⁻¹: 1700 m.p. 88.3~90.1° C. |
| 26 | Cl | Cl | 3-F | NMR(400MHz, CDCl₃)δ ppm: 0.97(3H, t, J=7.3Hz), 1.50-1.60(1H, m), 1.70-1.79 (1H, m), 2.41-2.47(1H, m), 3.46-3.53(2H, m), 3.93-3.97(1H, m), 6.93-7.03 (3H, m), 7.31-7.36(1H, m), 7.42(1H, d, J=8.8Hz), 7.59(1H, dd, J=2.2Hz, J=8.8Hz), 7.84(1H, d, J=2.9Hz) IRνKBr cm⁻¹: 1705 m.p. 107.0~108.0° C. |
| 27 | CH₃ | Cl | 3-F | NMR(400MHz, CDCl₃)δ ppm: 0.97(3H, t, J=7.3Hz), 1.50-1.58(1H, m), 1.71-1.78 (1H, m), 2.35(3H, s), 2.40-2.46(1H, m), 3.45-3.54(2H, m), 3.93-3.98 (1H, m), 6.95-7.04(3H, m), 7.21(1H, d, J=8.8Hz), 7.30-7.36(1H, m), 7.52 (1H, dd, J=2.2Hz, J=8.8Hz), 7.67(1H, d, J=2.2Hz) IRνKBr cm⁻¹: 1705 m.p. 101.9~102.8° C. |
| 28 | H | C₂H₅ | 3-F | NMR(400MHz, CDCl₃)δ ppm: 0.97(3H, t, J=7.3Hz), 1.25(3H, t, J=8.1Hz), 1.51-1.62 (1H, m), 1.70-1.79(1H, m), 2.39-2.47(1H, m), 2.66(1H, dd, J=8.1Hz, J=15.4Hz), 3.47(1H, d, J=10.3Hz), 3.55-3.59(1H, m), 4.00(1H, dd, J=8.1Hz, J=9.5Hz) 6.96-7.06(4H, m), 7.25-7.36(2H, m), 7.42(1H, dd, J=1.5Hz, J=8.1Hz), 7.58(1H, s) IRνneat cm⁻¹: 1700 |
| 29 | CH₃ | CH₃ | 3-F | NMR(400MHz, CDCl₃)δ ppm: 0.96(3H, t, J=7.3Hz), 1.51-1.60(1H, m), 1.71-1.78 (1H, m), 2.24(3H, s), 2.28(3H, s), 2.38-2.44(1H, m), 3.46(1H, d, J=10.3Hz), 3.53-3.57(1H, m), 3.96(1H, dd, J=7.3Hz, J=9.5Hz), 6.96-6.99(2H, m), 7.05(1H, d, J=7.3Hz), 7.12(1H, d, J=8.1Hz), 7.30-7.35(2H, m), 7.48(1H, d, J=2.2Hz) IRνKBr cm⁻¹: 1700 m.p. 92.6~94.1° C. |
| 30 | H | F | 3-F | NMR(400MHz, CDCl₃)δ ppm: 0.97(3H, t, J=7.3Hz), 1.59-1.66(1H, m), 1.72-1.77 (1H, m), 2.40-2.50(1H, m), 3.48-3.56(2H, m), 4.00(1H, dd, J=7.8Hz, J=9.3Hz), 6.84-6.89(1H, m), 6.96-7.05(3H, m), 7.30-7.42(3H, m), 7.56-7.60(1H, m) IRνKBr cm⁻¹: 1705 m.p. 59.0~60.2° C. |
| 31 | H | F | 3-CF₃ | NMR(400MHz, CDCl₃)δ ppm: 0.96-0.99(3H, m), 1.53-1.65(1H, m), 1.69-1.81 (1H, m), 2.40-2.52(1H, m), 3.51-3.63(2H, m), 3.96-4.08(1H, m), 6.86-6.93 (1H, m), 7.29-7.70(7H, m) IRνKBr cm⁻¹: 1705 m.p. 83.2~84.1° C. |
| 32 | H | CN | 3-F | NMR(400MHz, CDCl₃)δ ppm: 0.98(3H, t, J=7.3Hz), 1.51-1.66(1H, m), 1.72-1.81 (1H, m), 2.45-2.53(1H, m), 3.51(1H, d, J=10.3Hz), 3.55-3.59(1H, m), 4.01(1H, dd, J=7.8Hz, 9.3Hz), 6.96-7.04(3H, m), 7.32-7.36(1H, m), 7.40-7.50(2H, m), 7.98-8.02(2H, m) IRνneat cm⁻¹: 1710, 2230  n_D (19.6° C.): 1.576 |
| 33 | H | NO₂ | 3-F | NMR(400MHz, CDCl₃)δ ppm: 1.00(3H, t, J=7.3Hz), 1.57-1.68(1H, m), 1.74-1.82 (1H, m), 2.49-2.54(1H, m), 3.53(1H, d, J=10.0Hz), 3.61-3.65(1H, m), 4.05-4.10(1H, m), 6.97-7.09(3H, m), 7.33-7.39(2H, m), 7.55(1H, t, 8.3Hz), 8.00-8.03(1H, m), 8.27(1H, dd, J=2.0Hz, 8.3Hz), 8.39(1H, t, J=2.0Hz) IRνKBr cm⁻¹: 1705 m.p. 107.1~109.5° C. |
| 34 | H | CH₃O | 3-F | NMR(400MHz, CDCl₃)δ ppm: 0.97(3H, t, J=7.4Hz), 1.50-1.64(1H, m), 1.72-1.80 (1H, m), 2.39-2.50(1H, m), 3.48(1H, d, J=10.0Hz), 3.53-3.57(1H, m), |

TABLE 1-continued

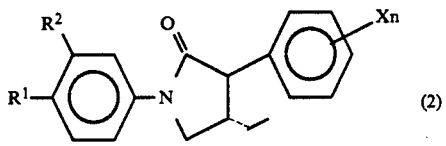

| Compound No. | Substituents of General Formula (2) R₁ | R₂ | Xn | Values of Physical Properties |
|---|---|---|---|---|
| | | | | 3.82(3H, s), 4.00(1H, dd, J=8.0Hz, J=9.6Hz), 6.72(1H, dd, J=2.2Hz, J=8.2Hz) 6.97-7.02(2H, m), 7.05(1H, d, J=7.2Hz), 7.12(1H, dd, J=1.2Hz, J=8.0Hz), 7.25-7.36(2H, m), 7.49(1H, t, J=2.2Hz) IR$\nu$neat cm$^{-1}$: 1700 |
| 35 | H | OH | 3-F | NMR(400MHz, CDCl$_3$)$\delta$ ppm: 0.95(3H, t, J=7.3Hz), 1.48-1.59(1H, m), 1.65-1.79 (1H, m), 2.35-2.45(1H, m), 3.50-3.56(2H, m), 4.00(1H, dd, J=8.1Hz, J=9.5Hz), 6.60(1H, dd, J=2.2Hz, J=8.1Hz), 6.85(1H, dd, J=1.5Hz, J=8.1Hz), 6.95-7.06(3H, m), 7.18(1H, t, J=8.1Hz), 7.29-7.34(1H, m), 7.64(1H, t, J=2.2Hz) IR$\nu$KBr cm$^{-1}$: 1665, 3250  m.p. 116~124° C. |
| 36 | H | PhO | 3-F | NMR(400MHz, CDCl$_3$)$\delta$ ppm: 0.95(3H, t, J=7.6Hz), 1.50-1.62(1H, m), 1.69-1.80 (1H, m), 2.38-2.49(1H, m), 3.46-3.55(2H, m), 3.98(1H, dd, J=7.8Hz, 9.0Hz), 6.80(1H, dd, J=1.6Hz, 8.0Hz), 6.95-7.11(6H, m), 7.30-7.40(5H, m), 7.47(1H, dd, J=1.6Hz, 8.0Hz) IR$\nu$KBr cm$^{-1}$: 1700 |
| 37 | H | H | 3-F | NMR(400MHz, CDCl$_3$)$\delta$ ppm: 0.97(3H, t, J=7.3Hz), 1.52-1.59(1H, m), 1.72-1.79 (1H, m), 2.40-2.46(1H, m), 3.49(1H, d, J=10.5Hz), 3.55-3.60(1H, m), 4.01(1H, dd, J=7.3Hz, 9.5Hz), 6.97-7.06(3H, m), 7.17(1H, t, J=7.3Hz), 7.30-7.40 (3H, m), 7.66-7.68(2H, m) IR$\nu$KBr cm$^{-1}$: 1700  m.p. 87.5~89.0° C. |
| 38 | H | iso-Pr | 3-F | NMR(400MHz, CDCl$_3$)$\delta$ ppm: 0.97(3H, t, J=7.3Hz), 1.26(6H, d, J=6.8Hz), 1.51~1.62 (1H, m), 1.70~1.80(1H, m), 2.38~2.50(1H, m), 2.86~2.96(1H, m) 3.48(1H, d, J=10.4Hz), 3.58(1H, t, J=9.2Hz), 4.01(1H, t, J=9.2Hz), 6.96~7.07 (4H, m), 7.25~7.41(3H, m), 7.57~7.64(1H, m) IR$\nu$nujol (cm$^{-1}$): 1695  m.p. 58.5~60.0° C. |
| 39 | H | iso-Pr | 3,5-F$_2$ | NMR(400MHz, CDCl$_3$)$\delta$ ppm: 0.98(3H, t, J=7.3Hz), 1.26(6H, d, J=6.8Hz), 1.51~1.58 (1H, m), 1.70~1.77(1H, m), 2.37~2.42(1H, m), 2.89~2.94(1H, m) 3.44(1H, d, J=10.3Hz), 3.58(1H, t, J=8.8Hz), 3.98(1H, t, J=8.8Hz), 6.98~7.39 (6H, m), 7.55~7.64(1H, m) IR$\nu$neat (cm$^{-1}$): 1699 |
| 40 | H | iso-Pr | 3,4-F$_2$ | NMR(400MHz, CDCl$_3$)$\delta$ ppm: 0.98(3H, t, J=7.3Hz), 1.26(6H, d, J=6.6Hz), 1.53~1.60 (1H, m), 1.72~1.77(1H, m), 2.40~2.44(1H, m), 2.89~2.96(1H, m) 3.47(1H, d, J=10.3Hz), 3.58(1H, t, J=9.2Hz), 3.99(1H, t, J=9.2Hz), 6.72~6.85 (3H, m), 7.04~7.55(3H, m), 7.61~7.63(1H, m) IR$\nu$nujol (cm$^{-1}$): 1687  m.p. 77.0~79.0° C. |
| 41 | H | iso-Pr | 3-Cl | NMR(400MHz, CDCl$_3$)$\delta$ ppm: 0.97(3H, t, J=7.6Hz), 1.26(6H, d, J=6.6Hz), 1.50~1.61 (1H, m), 1.71~1.78(1H, m), 2.41~2.50(1H, m), 2.92(1H, sept, J=6.6Hz), 3.46(1H, d, J=10.3Hz), 3.58(1H, t, J=9.2Hz), 4.11(1H, t, J=9.2Hz), 7.05(1H, d, J=8.0Hz), 7.16(1H, d, J=7.3Hz), 7.22~7.41(5H, m), 7.64(1H, d, J=2.2Hz) IR$\nu$nujol (cm$^{-1}$): 1704  m.p. 88.5~90.0° C. |
| 42 | H | iso-Pr | 3-Br | NMR(400MHz, CDCl$_3$)$\delta$ ppm: 0.97(3H, t, J=7.6Hz), 1.26(6H, d, J=6.6Hz), 1.52~1.59 (1H, m), 1.71~1.76(1H, m), 2.38~2.50(1H, m), 2.89~2.94(1H, m) 3.45(1H, d, J=10.3Hz), 3.57(1H, dd, J=8.8Hz, 9.5Hz), 4.00(1H, dd, J=8.1Hz, 8.89Hz), 7.04(1H, d, J=7.3Hz), 7.15~7.43(6H, m), 7.64(1H, s) IR$\nu$Kbr (cm$^{-1}$): 1700  m.p. 82.0~83.2° C. |

COMPARATIVE EXAMPLE 1

Synthesis of 4-ethyl-3-(3-chlorophenyl)-1-(3-isopropylphenyl)pyrrolidine-2-one 5.0 g (14.7 mmol) of 4-ethyl-3-(3-chlorophenyl)-1-(3-isopropylphenyl)-3-pyrroline-2-one synthesized in Example 4 were dissolved in 50 ml of ethanol, and 0.56 g (14.7 mmol) of sodium boron hydride were added thereto little by little at room temperature under stirring. Reaction was further allowed to proceed at the same temperature for 1 hour, and the reaction mixture was then poured into 1 N hydrochloric acid, followed by extraction with ethyl acetate. The resultant organic layer was washed with water, an aqueous saturated sodium bicarbonate solution and water in this order, and then dried over magnesium sulfate. Next, the solvent was distilled off under reduced pressure. The resultant residue was analyzed by high-speed liquid chromatography (column: YMC-A302 (ODS), mobile phase: MeCN/H$_2$O=9/1 (v/v), UV: 254 nm), and as a result, it was apparent that the residue was a mixture of the starting material/the end product=3/1 and a large amount of the raw material remained.

In this comparative example, the reducing reaction with sodium boron hydride in Example 7 was carried out under usual conditions, and therefore the results of the comparative example indicate that the yield of the end product largely decreases.

Next, formulation examples and herbicidal activity tests of certain herbicides the active ingredients of which were prepared according to the present invention will be described.

FORMULATION EXAMPLE 1 (WETTABLE POWDER)

A wettable powder was obtained by sufficiently grinding and mixing 20 parts by weight of Compound No. 3 of the present invention, 2 parts by weight of Neopelex (trade name, made by Kao Corporation; sodium dodecyl benzene sulfonate), 1 parts by weight of Neugen EA80 (trade name, made by Sanyo Chemical Industries, Ltd.; polyoxyethylene nonylphenyl ether), 5 parts by weight of white carbon and 72 parts by weight of diatomaceous earth.

FORMULATION EXAMPLE 2 (WETTABLE POWDER)

A wettable powder was obtained by sufficiently grinding and mixing 20 parts by weight of Compound No. 17 of the present invention, 2 parts by weight of sodium alkylbenzenesulfonate, 1 part by weight of a polyoxyethylene alkylphenyl ether and 77 parts by weight of Giecrite.

FORMULATION EXAMPLE 3 (WETTABLE POWDER)

A wettable powder was obtained by thoroughly grinding and mixing 50 parts by weight of Compound No 41 of the present invention, 5 parts by weight of white carbon, 6 parts by weight of polyoxyethylene alkylphenyl ether ammonium sulfate, 2 parts by weight sodium lignine sulfonate and 37 parts by weight of diatomaceous earth by the use of a jet-0-mizer.

FORMULATION EXAMPLE 4 (FLOWABLE FORMULATION)

A flowable formulation was obtained by adding 91.7 parts by weight of water to 5 parts by weight of Compound No. 17 of the present invention, 2 parts by weight of sodium lignine sulfonate, 0.3 part by weight of xanthane gum and 1 part by weight of a polyoxyethylene alkylaryl ether, mixing them, and then finely grinding the mixture by the use of a sand grinder.

FORMULATION EXAMPLE 5 (FLOWABLE FORMULATION)

A flowable formulation was obtained by wet grinding and mixing 30 parts by weight of Compound No. 41 of the present invention and a solution of 10 parts by weight of Sun Ekisu P252 (trade name, made by Sanyo-Kokusaku Pulp Co., Ltd.; sodium lignine sulfonate) in 50 parts by weight of water, and then adding and mixing a solution of 0.2 part by weight of Kelzan S (trade name, made by Kelco Corp.; xanthan gum) in 9.6 parts by weight of water and 0.2 part by weight of Deltop (trade name, made by Takeda Chemical Industries, Ltd.; organic iodine fungicide).

FORMULATION EXAMPLE 6 (POWDER)

A powder was obtained by thoroughly grinding and mixing 1 part by weight of Compound No. 17 of the present invention, 0.5 part by weight of Emulgen 910 (trade name, made by Kao Corporation; polyoxyethylene nonylphenyl ether) and 98.5 parts by weight of kaolin clay.

FORMULATION EXAMPLE 7 (POWDER)

A powder was obtained by mixing and grinding 3 parts by weight of Compound No. 41 of the present invention, 3 parts by weight of sodium lignine sulfonate, 2 parts by weight of a polyoxyethylene alkylaryl ether and 92 parts by weight of clay.

FORMULATION EXAMPLE 8 (DRY FLOWABLE FORMULATION)

A dry flowable formulation was obtained by mixing 60 parts by weight of finely ground Compound No. 41 of the present invention, 5 parts by weight of a sodium alkylbenzenesulfonate and 35 parts by weight of a polypropylene glycol polyethylene glycol ether.

FORMULATION EXAMPLE 9 (GRANULES)

0.3 part by weight of Compound No. 17 of the present invention, 2 parts by weight of Neopelex (trade name, as described above), 2 parts by weight of Sun Ekisu P252 (trade name as described above), 72.7 parts by weight of bentonite and 23 parts by weight of talc were thoroughly mixed. A suitable amount of water was added to the resultant mixture to wet the same, followed by extrusion of the mass through a small injection molding machine into pellets. After the pellets were dried at 30°-60° C. in air and then crushed into granules, the granules were then classified by a sifting machine to collect granules of 0.3-2 mm.

FORMULATION EXAMPLE 10 (GRANULES)

0.5 part by weight of Compound No. 41 of the present invention, 2 parts by weight of Gosenol GL-05s (PVA made by Nippon Synthetic Chemical Industry Co., Ltd.), 2 parts of Sun Ekisu P252 (trade name as described above) and 95.5 parts of clay were thoroughly mixed, and a suitable amount of water was then added to the mixture to wet the same, followed by extrusion of the mass through an injection molding machine into pellets. After the pellets were dried at 60°-90° C. in air and then crushed into granules, the granules were then classified by a sifting machine to collect granules of 0.3-1 mm.

FORMULATION EXAMPLE 11 (EMULSION)

An emulsion was obtained by mutually mixing and then dissolving 10 parts by weight of Compound No. 3 of the present invention, 10 parts by weight of Sorpole 800A (trade name, made by Toho Chemical Industries Co., Ltd.; a nonionic/anionic surfactant mixture) and 80 parts by weight of o-xylene.

TEST 1 TREATMENT OF SOIL UNDER SUBMERGED CONDITION (PRE-EMERGENCE TREATMENT)

1/5000-are Wagner pots were filled with soil. Seeds or tubers of *Echinochloa crusoalli*, bulrush (*Scirpus juncoides*), *Sagittaria pygmaea*, monochoria (*Monochoria vaginalis*), water nutgrass (*Cyperus serotinus*) and false pimpernel (*Lindernia pyxidaria*) were sown or planted under submerged condition. Two pairs of rice (*Oryza sativa*) seedlings (2-3 leaf stage), which had been reared in advance, were transplanted to each pot and were allowed to grow in a green house. Each pair consisted of two rice seedlings. One day later (before emergence of weeds), each pot was treated with granules which had been prepared by processing a predetermined amount of the test compound in accordance with the procedure described in Formulation Example 9. The growing state of weeds and the injurious state to rice were observed 30 days later. The results are summarized in Table 2.

In the table, the damage degree of each test plant and the injurious degree to rice were determined by comparing the growing state of the test plant and rice with that of the corresponding plant and rice in untreated pots, and they are denoted in accordance with the following standard.

| Rank | Growth Rate (%)* | Degree of Damage |
|---|---|---|
| 5 | 0-5 | Death |
| 4 | 6-10 | Severe damages |
| 3 | 11-40 | Medium damages |
| 2 | 41-70 | Small damages |
| 1 | 71-90 | Slight damages |
| 0 | 91-100 | No damages |

*The growth rate (%) was expressed in terms of the percentage of dry weight relative to the dry weight of untreated group.

Comparative Compounds A and B in Table 2 are the following compounds: A: 1-(3-trifluoromethylphenyl)-3-chloro-4-chloromethylpyrrolidine-2-one. B: 4-chloromethyl-3-(3-chlorophenyl)-1-(3-trifluoromethyl)-pyrrolidine-2-one.

TABLE 2

Treatment of Soil under Submerged Condition (Pre-emergence Treatment)

| Compound No. | Application rate, kg/ha | Echinochloa crusgalli | Monochoria (Monochoria vaginalis) | Bulrush (Scirpus juncoides) | False pimpernel (Lindernia pyxidaria) | Rice (Oryza sativa) |
|---|---|---|---|---|---|---|
| 3 | 0.03 | 5 | 5 | 3 | 5 | 0 |
|   | 0.05 | 5 | 5 | 4 | 5 | 0 |
|   | 0.1 | 5 | 5 | 5 | 5 | 1 |
| 17 | 0.03 | 5 | 5 | 3 | 5 | 0 |
|   | 0.05 | 5 | 5 | 4 | 5 | 0 |
|   | 0.1 | 5 | 5 | 5 | 5 | 1 |
| 41 | 0.03 | 5 | 3 | 2 | 5 | 0 |
|   | 0.05 | 5 | 4 | 3 | 5 | 0 |
|   | 0.1 | 5 | 5 | 5 | 5 | 0 |
| Compound A | 0.03 | 0 | 0 | 0 | 0 | 0 |
|   | 0.05 | 1 | 1 | 1 | 2 | 1 |
|   | 0.1 | 2 | 3 | 2 | 3 | 2 |
| B | 0.03 | 0 | 0 | 0 | 0 | 0 |
|   | 0.05 | 3 | 2 | 1 | 2 | 0 |
|   | 0.1 | 5 | 5 | 4 | 4 | 0 |

In these tests, as compared with Comparative Agents A and B, the herbicidal compositions regarding the present invention exerted higher herbicidal effects to the sample weeds in the paddy fields in spite of the low application rates, and they also exerted excellent safety to the rice.

TEST 2 TREATMENT OF SOIL UNDER SUBMERGED CONDITION (GROWING PERIOD TREATMENT)

1/5000-are Wagner pots were filled with soil. Seeds of Echinochloa crusgalli, bulrush (Scirpus juncoides), monochoria (Monochoria vaginalis) and false pimpernel (Lindernia pyxidaria) were sown under submerged condition. Two pairs of rice (Oryza sativa) seedlings (2-3 leaf stage), which had been reared in advance, were transplanted to each pot and were allowed to grow in a green house. Each pair consisted of two rice seedlings. When barnyard grass became bifoliate, each pot was treated with granules which had been prepared by processing a predetermined amount of the test compound in accordance with the procedure described in Formulation Example 10. The emergence state of weeds and the injurious state to rice were observed 30 days later. The results are summarized in Table 3. In the table, the damage degree of each test plant and the injurious degree to rice were determined in the same manner as in Test 1.

TABLE 3

Treatment of Soil under Submerged Condition (Pre-emergence Treatment)

| Compound No. | Application rate, kg/ha | Echinochloa crusgalli | Monochoria (Monochoria vaginalis) | Bulrush (Scirpus juncoides) | False pimpernel (Lindernia pyxidaria) | Rice (Oryza sativa) |
|---|---|---|---|---|---|---|
| 3 | 0.13 | 5 | 4 | 2 | 5 | 0 |
|   | 0.25 | 5 | 5 | 4 | 5 | 0 |
|   | 0.5 | 5 | 5 | 5 | 5 | 1 |
| 17 | 0.13 | 5 | 4 | 3 | 5 | 0 |
|   | 0.25 | 5 | 5 | 4 | 5 | 0 |
|   | 0.5 | 5 | 5 | 5 | 5 | 1 |
| 41 | 0.13 | 4 | 3 | 2 | 5 | 0 |
|   | 0.25 | 5 | 4 | 3 | 5 | 0 |
|   | 0.5 | 5 | 5 | 5 | 5 | 0 |
| Compound A | 0.13 | 0 | 0 | 0 | 0 | 0 |
|   | 0.25 | 1 | 1 | 0 | 2 | 2 |
|   | 0.5 | 2 | 2 | 1 | 2 | 3 |
| B | 0.13 | 0 | 0 | 0 | 0 | 0 |
|   | 0.25 | 2 | 1 | 1 | 1 | 0 |

TABLE 3-continued

| | Treatment of Soil under Submerged Condition (Pre-emergence Treatment) | | | | |
|---|---|---|---|---|---|
| Application rate, kg/ha | Echinochloa crusgalli | Monochoria (Monochoria vaginalis) | Bulrush (Scirpus juncoides) | False pimpernel (Lindernia pyxidaria) | Rice (Oryza sativa) |
| 0.5 | 3 | 2 | 2 | 3 | 0 |

In these tests, as compared with Comparative Agents A and B, the herbicidal compositions regarding the present invention exerted higher herbicidal effects to the sample weeds in the paddy fields in spite of the low application rates, and they also exerted excellent safety to the rice.

What is claimed is:

1. A method for preparing 3,4-trans-4-ethyl-1,3-disubstituted (substituted phenyl) pyrrolidine-2-one represented by the formula (1)

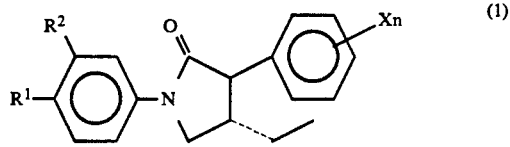
(1)

wherein $R^1$ is a hydrogen atom, halogen atom or methyl group; $R^2$ is a hydrogen atom, alkyl group having 1 to 3 carbon atoms, alkoxy group having 1 to 4 carbon atoms, nitro group, cyano group, phenoxy group, hydroxyl group or halogen atom; X is a hydrogen atom, halogen atom, trifluoromethyl group, alkyl group having 1 to 3 carbon atoms, cyano group or nitro group; and n is 1 or 2 and denotes the number of substituents represented by X, and in the case of N=2, the substituents of X may be identical or different, but $R^1, R^2$ and Xn are not simultaneously hydrogen atoms, which comprises: reducing 4-ethyl-1,3-disubstituted (substituted phenyl)-3-pyrroline-2-one represented by the formula (2)

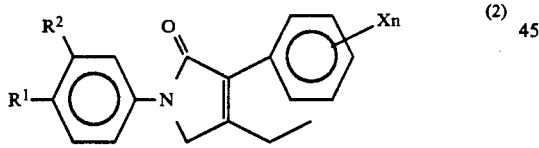
(2)

wherein $R^1, R^2$, X and n are as defined above, with sodium boron hydride in the presence of methanol in an inert solvent.

2. The method for preparing 3,4-trans-4-ethyl-1,3-disubstituted(substituted phenyl)pyrrolidine-2-one of claim 1, wherein the reduction is conducted by adding sodium boron hydride to 4-ethyl-1,3-disubstituted(substituted phenyl)-3-pyrroline-2-one represented by the formula (2) dissolved in the inert solvent, and then slowly adding methanol thereto under heating.

3. The method for preparing 3,4-trans-4-ethyl-1,3-disubstituted(substituted phenyl)pyrrolidine-2-one of claim 2, wherein the amount of sodium boron hydride is in the range of from 0.5 to 1.0 mol per mol of 4-ethyl-1,3-disubstituted(substituted phenyl)-3-pyrroline-2-one represented by the formula (2).

4. The method for preparing 3,4-trans-4-ethyl-1,3-disubstituted(substituted phenyl)pyrrolidine-2-one of claim 2 wherein the amount of methanol to be added is in the range of from 0.2 to 2.0 ml.

5. The method for preparing 3,4-trans-4-ethyl-1,3-disubstituted(substituted phenyl)pyrrolidine-2-one of claim 2 wherein the amount of sodium boron hydride is in the range of from 0.5 to 1.0 mol per mol of 4-ethyl-1,3-disubstituted(substituted phenyl)-3-pyrroline-2-one represented by the formula (2), and the amount of methanol to be added is in the range of from 0.2 to 2.0 ml.

6. A method for preparing 3,4-trans-4-ethyl-1,3-disubstituted(substituted phenyl)pyrrolidine-2-one, which comprises:

1) reacting 3,4-disubstituted aniline represented by formula (3)

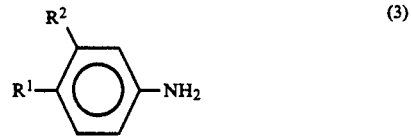
(3)

wherein $R^1$ is a hydrogen atom, halogen atom or methyl group; and $R^2$ is a hydrogen atom, alkyl group having 1 to 3 carbon atoms, trifluoromethyl group, haloalkoxy group having 1 to 3 carbon atoms, alkoxy group having 1 to 4 carbon atoms, nitro group, cyano group, phenoxy group, hydroxyl group or halogen atom, with a haloketone represented by formula (4)

(4)

wherein Y is a halogen atom, to obtain a ketoaniline derivative represented by formula (5)

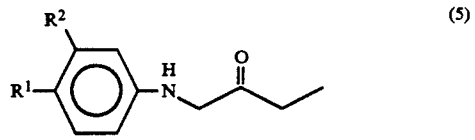
(5)

wherein $R^1$ and $R^2$ are as defined above, 2) acylating the ketoaniline derivative with an Xn-substituted phenylacetyl halide to obtain a carbonyl derivative represented by formula (6)

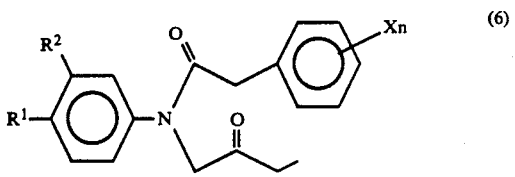
(6)

wherein R¹ and R² are as defined above, X is a hydrogen atom, halogen atom, trifluoromethyl group, alkyl group having 1 to 3 carbon atoms, cyano group or nitro group; and n is 1 or 2 and denotes the number of substituents represented by X, and in the case of n=2, the substituents of X may be identical or different, but R¹,R² and Xn are not simultaneously hydrogen atoms, 3) treating the carbonyl derivative with a base to carry out an intramolecular aldol condensation, thereby producing 4-ethyl-1,3-disubstituted(substituted phenyl)-3-pyrroline-2-one represented by formula (2)

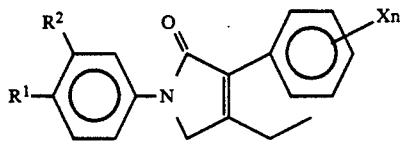

wherein R¹,R² X and n are defined above, and 4) reducing the 4-ethyl-1,3-disubstituted(substituted phenyl)-3-pyrroline-2-one with sodium boron hydride in the presence of methanol in an inert solvent, to obtain 3,4-trans-4-ethyl-1,3-disubstituted(substituted phenyl)pyrrolidine-2-one of formula (1)

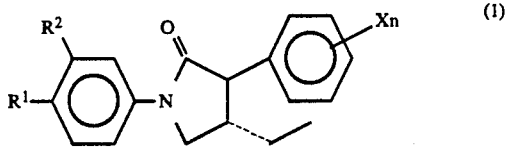

wherein R¹,R², X and n are as defined above.

7. The method for preparing 3,4-trans-4-ethyl-1,3-disubstituted(substituted phenyl)pyrrolidine-2-one according to claim 5, wherein steps 1 and 2 are conducted in the presence of a base in a solvent.

* * * * *